(12) United States Patent
Seex

(10) Patent No.: US 10,098,622 B2
(45) Date of Patent: Oct. 16, 2018

(54) RETRACTOR BLADE AND ASSEMBLY FOR SPINAL SURGERY

(75) Inventor: Kevin Seex, Kingswood (AU)

(73) Assignee: RETROSPINE PTY LTD, New South Wales (AU)

( * ) Notice: Subject to any disclaimer, the term of this patent is extended or adjusted under 35 U.S.C. 154(b) by 1227 days.

(21) Appl. No.: 13/059,479

(22) PCT Filed: Aug. 17, 2009

(86) PCT No.: PCT/AU2009/001053
§ 371 (c)(1),
(2), (4) Date: Apr. 9, 2012

(87) PCT Pub. No.: WO2010/019991
PCT Pub. Date: Feb. 25, 2010

(65) Prior Publication Data
US 2012/0271120 A1    Oct. 25, 2012

(30) Foreign Application Priority Data
Aug. 18, 2008  (AU) ................................ 2008904242

(51) Int. Cl.
  *A61B 1/32*    (2006.01)
  *A61B 17/02*   (2006.01)
(52) U.S. Cl.
  CPC ...... *A61B 17/02* (2013.01); *A61B 2017/0256* (2013.01)
(58) Field of Classification Search
  CPC ................. A61B 17/02; A61B 2017/0256
  See application file for complete search history.

(56) References Cited

U.S. PATENT DOCUMENTS

| 6,416,465 B2 | 7/2002 | Brau |
| 6,692,434 B2 * | 2/2004 | Ritland ............ A61B 17/02 600/210 |
| 7,481,766 B2 | 1/2009 | Lee et al. |
| 2004/0236341 A1 | 11/2004 | Petersen |
| 2005/0080320 A1 * | 4/2005 | Lee et al. .................. 600/214 |
| 2005/0154395 A1 | 7/2005 | Robbins et al. |
| 2008/0234550 A1 | 9/2008 | Hawkes et al. |
| 2011/0130634 A1 * | 6/2011 | Solitario, Jr. ...... A61B 17/3421 600/231 |

OTHER PUBLICATIONS

International Search Report for PCT/AU2009/001053.

* cited by examiner

*Primary Examiner* — David Isabella
*Assistant Examiner* — Christine Nelson
(74) *Attorney, Agent, or Firm* — B. Aaron Schulman; Stites & Harbison PLLC

(57) ABSTRACT

A retractor blade comprising a blade body having first and second ends, the first end including means to allow connection of the blade body to a support member, the second end including a first part disposed in a first plane and a second part disposed in a second plane, wherein the first and second parts are orthogonal and at least one of said first and second parts terminates in an end at least part of which includes a contour which generally conforms to a contour of a spinal vertebrae.

14 Claims, 10 Drawing Sheets

RETRACTOR BLADE AND ASSEMBLY FOR SPINAL SURGERY

BACKGROUND

The present invention relates to retraction assemblies used for retracting soft tissue in surgery close to the bone. More particularly, the invention relates to a retracting blade having a geometry which engages vertebral bone during retraction of soft tissues to enable safer and more convenient retraction of those tissues. The invention further provides a retraction blade having a formation at a distal end which at least partially conforms to bone contour and transfers loading to vertebral bone and means at a proximal end to engage a support member. The invention further provides a retractor blade in which the formation at the distal end allows retraction of veins and arteries during a rotational movement about an axis through the spine. Although the invention is described below in relation to the anterior lumbar spine, the principles and geometry embodied in the retractor blade have applications throughout the spine and wherever bone is available to provide support.

PRIOR ART

There are in existence a number of assemblies used in retraction of soft tissues and which include retractor blades which engage bone during such retraction. In particular, there are known retractor blades which retract soft tissue during spinal surgery. Such retractor blades are maintained at a setting to allow a surgeon access to a spinal disc space and vertebrae in cervical and lumbar spinal disc surgery.

Retractors are sometimes used in conjunction with distraction assemblies. The process of separating bones is termed distraction. This involves insertion of a spreading type instrument into an excised disc space which engages the upper and lower vertebral bodies and when applied separates them. This is known as intervertebral distraction. Alternatively, in the cervical spine, in a procedure known as non-intervertebral distraction may be used in which long screws are inserted into the upper and lower vertebral bodies. Surrounding soft tissues must be held apart by retractors. Once retracted, there is a natural elastic recoil of the stretched tissues so it is essential to employ retractors which effectively restrain soft tissues and without loosing the requisite retraction.

It is important to reduce trauma to soft tissues which may occur from contact with parts of retractor blades so that the surgical procedure is as minimally invasive as possible and thus minimally interferes with and minimally traumatizes the organs, tissues and vasculature being displaced to allow access to the vertebral region being treated. Posterior surgery can utilize larger retractors since the insertion space is more accommodating and posterior structures requiring retraction such as muscles, are less sensitive. Various types of retractors are known each having means to enable retention by a support member.

Anterior lumbar surgery can be performed for a number of reasons, but most commonly this is for excision of degenerate intervertebral disc after which a fusion procedure or lumbar disc arthroplasty is performed. It is recognized by spinal surgeons that the most difficult and dangerous part of the surgery on the anterior lumbar disc spaces is dissection, mobilization and maintenance of retraction of the vessels, and in particular the left common iliac vein. In the usual left retroperitoneal approach to the spine, this vein has to be retracted from left to right and inferiorly to expose the inferior right hand corner of the 45 disc space. Whatever level of surgery is being performed, there is an initial approach requiring some degree of vascular dissection. The approach and surgery generally requires the use of handheld retractors, at least initially, which may then be replaced with fixed retractors to maintain retraction for the rest of the procedure.

Fixed retractors require either internal fixation to spinal vertebra or external fixation using a table mounted system. Retractors are usually positioned to hold tissues away from the surgical field both laterally (side to side) and longitudinally (up and down) relative to a spine. It is the lateral retraction that represents the greatest difficulty requiring a solution.

Existing retractors may be internally or externally fixed. Internal fixation of retractors is utilized to hold the left common iliac vein or other tissues in a retracted position. There is a danger that veins may be punctured or squeezed. Due to the difficulty and dangers of moving and keeping the blood vessels retracted during anterior lumbar surgery, stability of the retractors is particularly important. The most stable retractors are those embedded in the bone e.g. Steinman pins and Hohmann retractors. Steinman pins are long pins impacted into the bone while Hohmann retractors are conventional retractor blades with a curved pointed end which can be impacted into the bone for stability. Some limited movement of the Hohmann blade is possible by bending. Also known are standard retractor blades that have a channel that allow separate introduction of sharp pins through the channel into the vertebral body thus securing the blade to the spine.

Internally fixed retractors have limitations. Although very stable once in place they are not adjustable and insertion does produce bone injury. Insertion and removal can also be hazardous to vessels or other soft tissues.

External fixation of retractors is achieved by the use of table mounted retractors. Various table mounted retractor systems are available e.g. Thomson, Omnitract, Bookwalter and Synframe. The table based systems (see FIG. 1 below), offer a variety of retractor blades for holding back the tissues connected to a table mounted ring or support frame. Various shapes of blade are available. In order to improve on these and in particular to improve stability of these non internally fixed blades a new shape of retractor blade, called The Brau Blade, was developed. This blade is described in U.S. Pat. No. 6,416,465—(see FIG. 2h below).

That patent teaches an instrument and method for exposing a selected area of the anterior lumbar region for a surgical procedure on the spine comprising making an incision on a human or animal body that exposes the anterior rectus sheath of the left rectus muscle, cutting the anterior rectus sheath to expose the body of the rectus muscle, and mobilizing the rectus muscle along its length by at least 3 cm in both directions from the site of the sheath incision. The rectus is then retracted medially, and the posterior rectus sheath is incised to expose the peritoneum. The peritoneum is pushed aside and tissues between the surgeon and the psoas muscle are dissected away. The ureter and the left iliac vessels are mobilized so that they are retractable from the dissected field, then the rectus muscle is moved laterally and a retractor is inserted into the dissected field. The retractor comprises a handle portion and an elongated blade portion having a first end connected to the handle portion, and having a substantially flat configuration which generally extends at an angle relative to the handle and below an axis aligned with the handle when the retractor is in use in surgery. The blade portion also has a second end spaced from the handle portion and shaped as a lip which curves in a direction away from the handle portion. The lip projects to a remote end spaced less than about 2 cm from a plane defined by the blade portion adjacent to the lip. The retractor is stabilized by engaging the lateral aspect of a vertebral body or disc with the lip of the retractor and retracting the tissues with the blade portion to expose the selected vertebral area.

The Brau device is characterised in having a forward directed lip of the distal tip of the blade that curves forward away from the plane of the blade in an opposite direction to that of the handle, i.e towards the spine. This has a gently curved point or blunt lip that contacts the side of the spine and provides more stability than alternative blades during insertion of the retractor and possibly maintenance of retraction. It also has ridges in the lip to increase purchase with the side of the vertebral body or disc. It's gentle nose point increases the area of bone contact compared to Taylor Blades designed for use in the posterior lumbar spine, (Reference: G. Taylor, J B J Surgery vol 20,1, pp 183-184). Once positioned these blades are usually connected to an external table mounted frame.

The known externally fixed retractor blades have significant limitations.

1. Stability:

Contact and pressure on the blade against the bone improves stability of retractor blades. Most conventional blades however rely only on their external fixation for stability. If there is contact with the bone it lies at the side of the vertebral body usually at or above the equator of the vertebrae where the bone is curving postero-laterally. Although a vertebral body has a modest hour glass shape, it can, with minimal compromise of concept, be taken as having a cylindrical shape. The lip of the Brau blades and all other conventional blades when used for lateral retraction are in contact with the bone along the side of the body i.e. in contact with the spine along a superior inferior plane. To remain stable they rely on a solid immobile connection to the operating table through various linkages and if in contact with the bone, a force directed along the edge of the blade (the lip) parallel to this radius of the body. This stability is easily achieved when held in the hand, but not when attached to an external frame because of the moment arm from the end of the blade to the fixed anchorage at the side of the table: (see assembly of FIG. 1 below). Many conventional blades sit beside the bone with a lip curving away from the bone. Despite sophisticated linkages of the blades to their handles and their handles to the frame, it is mechanically difficult to keep immobile. In practice, once in position all table mounted retractor blades hold reasonably still relative to the table but not necessarily the spine. This is because they do not fix to the patient and when the patient's spine moves e.g. during impaction or positioning of implants, or other vigorous work, the lateral retractors tend to bounce and slip. In that case, soft tissues including vessels can slip under or around the retractor blades.

Contact with the bone by providing an additional point of stability helps reduce this, but even with the Brau retractor, it remains a problem. If a constant force is applied from the frame along the line of the blade, pushing the blade against the spine helps stability, but this can easily lead to the blade slipping or sliding posteriorly and causing tissue injury when the spine moves. Inadvertent downward pressure by surgeons or their assistants on these blades also is a problem as it leads to posterior displacement, because there is little or no support for the blade from the bone relying as it dies essentially on friction grip. This can lead to soft tissue injury.

By comparison when retracting longitudinally using retractor blades, the edge of the blades can be pushed down onto the anterior surface of the vertebral bodies where they are lying across the spine and perpendicular to the main radius. This gives them much greater relative stability. The stability is also enhanced because the anterior surface of the spine is less curved anteriorly than laterally.

An analogy to illustrate this difference in stability is to imagine rolling a heavy can of beans by pushing it with a ruler end on horizontally versus with the ruler end on but turned vertically. In addition to instability leading to tissue injury, it is also preferable to improve stability as this reduces the operating time lost spent adjusting retractors. In general terms the morbidity of surgery tends to increase with increasing length of procedure.

Bulging and Angular Tissue Distortion:

One of the limitations of all existing retraction systems is the tendency for the vessels, in particular the left common iliac vein, to bulge around the retractor, which can expose the vein to injury and impede the surgeon. This occurs at L5/S1 where the vessels are displaced superiorly and laterally and at L45 where this is inferiorly and laterally: Taken from "The Artificial Disc" by Buttner-Janz, Hochschuler and Mcafee. Published by Springer, 2003.

Various techniques can be employed to keep the vein safe, either by placing the lateral retractors as far laterally as possible displacing the vein laterally while retracting the vein inferiorly away from the disc space with another retractor. This technique risks over stretching the vein. Another technique is to fill the 'difficult corner' between the side to side and inferior blades with a swab or other protective material. Another approach is to displace the vein away with hand held retractors and insert a Steinman pin at the apex of the corner to maintain retraction. All of these techniques have the disadvantage that excessive retraction can lead to direct vessel injury, bleeding or thrombosis, and irregular retraction e.g. with pins produces angular distortion i.e. indenting the vein predisposing the patient to increased turbulent flow, and thereby thrombosis within the vessel. It is preferable to minimize the amount of retraction used and to use smooth retraction over an area, particularly when retracting blood vessels in order to reduce turbulence and thereby the potential for thrombosis within the vessel.

Numerous retractor blades exist for use in surgery of various shapes and geometry. One retractor blade is known with two surfaces at right angles to each other over the length of the blade. This is a handheld retractor for use posteriorly in the lumbar spine to retract muscle to aid in implantation of pedicle screws. This does not have any function to retract blood vessels. The end is shaped for bone contact on or close to the transverse processes of the spine or the sacrum without adapting to the anatomical shape of the bones and the bone contact is in one plane only.

There are other blade assemblies in the prior art such as that disclosed in U.S. Pat. No. 6,692,434 which discloses a method and device for a retractor for microsurgical intermuscular lumbar arthrodesis with a minimal approach which spares the lumbar muscles from surgical disruption and includes one of two retractor designs having blades angled approximately 90 degree with respect to each respective retractor handle. One blade is bent at an end portion thereof in a direction away from the handle portion. The other blade has first and second blade faces, with the second face having at least two toothed structures located thereon.

In another example of the prior art, a Retractor blade with curved distal edge that could be pressed against anterior lumbar spine (MAS Richardson Blade, Thomson retractor catalogue, FIG. 2 A) is known.

A combined distracter and retractor instrument for use during a spinal surgery procedure is disclosed in U.S. patent application No. 20050154395. The surgical instrument disclosed is configured to distract two adjacent vertebral elements and retract the nerve root to provide access to the distracted site. The instrument includes an elongated blade member having a wing located on an edge of the blade member, and a handle. This instrument is primarily for use in posterior access to the spine and is manually operated by a surgeon. The instrument has some soft tissue retracting capacity but is restricted in its use as it must be held by such persons as assistants and once located between vertebra must be rotated to procure any retraction.

Although there are a wide variety of retractor blades currently in use, in view of the disadvantages inherent in those blades, there remains room for improvement in the geometry of the blades with the objective of providing a blade which is easy to use, adaptable to existing support frames, efficiently maintains retraction of soft tissue and does not obstruct the surgeons path to the operating site and does not compromise retraction in the event of unwanted loading such as inadvertent bumping during surgery.

INVENTION

The present invention addresses the problems associated with the known retraction blades and seeks to improve the aforesaid prior art disadvantages of existing retractor systems by providing a retractor blade of the type supportable by a support structure, comprising adjustable support elements, the retractor blade including a distal end geometry which conforms at least in part to vertebral bone contours to facilitate stability and more effective and efficient soft tissue retraction during blade insertion and which efficiently distributes loads applied on the blade to the vertebrae for blade support during surgery.

This retractor according to the invention seeks to improve the stability of retractor blades during anterior lumbar surgery without requiring bone fixation. The invention provides an alternative blade shape that improves the quality retraction compared to existing systems and particularly retraction of blood vessels during L4/5 surgery. Although designed to aid surgery on the anterior lumbar spine the principles have application throughout the spine and elsewhere where bone is available for load distribution.

Since the co operation between the leading end geometry of the retractor blade of the present invention and the anatomical shape of the anterior aspects of lumbar vertebra is related to the functionality of the retractor blade, a brief description of relevant vertebral anatomy and its relevance to anterior lumbar surgery is described briefly below.

When viewed from above (axial section) the lumbar vertebral bodies are kidney shaped with a concavity posteriorly. The L5 vertebral body is more ovoid than other vertebrae. The anterior surface of all the vertebral bodies forms an approximate arc of a circle which is slightly flattened in the middle. The vertebral body diameter however varies. It is narrowest in the mid body and then expands circumferentially adjacent to the disc spaces between adjacent vertebra. When viewed in coronal section this produces a modest hour glass shape. In the axial plane the anterior oval vertebral shape is relatively constant with the discs and the endplates forming slightly larger diameter circles than in the mid body.

In its broadest form the present invention comprises:
a retractor blade comprising a blade body having first and second ends, the first end including means to allow connection of the blade body to a support member, the second end including a first part disposed in a first plane and a second part disposed in a second plane, wherein at least one of said first and second parts terminates in an edge at least part of which includes a contour which generally conforms to a contour of a spinal vertebrae.

In another broad form the present invention comprises:
an L shaped retractor blade for retracting soft tissues for spinal surgery, the retractor comprising: a blade body having first and second ends, the first end providing means to allow connection of the blade body to a support member, the second end comprising a first part disposed in a first plane and a second part disposed in a second plane normal to the first plane, wherein at least one of said first and second parts terminates in an edge at least part of which is capable of transmission of load applied to the retractor to spinal vertebrae to resist unwanted movement of the retractor.

In another broad form the present invention comprises:
a retractor blade comprising a blade body having first and second ends, the first end providing means to allow connection of the blade body to a support member, the second end comprising a first part disposed in a first plane and a second part disposed in a second plane, wherein at least one of said first and second parts terminates in an edge at least part of which includes a contour which generally conforms to a contour of a spinal vertebrae.

The first part in the first plane is essentially parallel to a longitudinal axis of the spine. The second part in the second plane is normal to the first plane. The contour of said edge of the second part defines an arc which generally conforms to a mid body circumferential surface of a lumbar vertebrae. According to a preferred embodiment, said edges of the first and second parts engage vertebral bone when an axial load is applied to the retractor.

According to one embodiment, the second part is formed by an abbreviation in the body of the blade. Preferably, the blade is formed as one piece and a majority of the body of the blade is disposed in the same plane as the first part.

In another broad form the present invention comprises:
a surgical retractor blade for retraction of soft tissue during anterior approach spinal surgery, the blade comprising: a generally elongated blade body having first and second ends, the first end providing means for connection of the blade body to a support member, the second end comprising a first part disposed in a first plane and a second part connected normal to the first part and disposed in a second plane, wherein each of said first and second parts terminate in respective continuous edges at least part of which include a concave contour which generally conforms to at least part of a contour of a spinal vertebrae, the second part further providing a load bearing edge which transmits loads applied to the blade to said vertebrae.

Preferably the second part is formed in the body of the blade by an abbreviation extending from the first end to a position beyond half the overall length of the blade body. Preferably, the body of the blade is substantially planar with the first part of the second end lying that plane. The second part of the second end is also preferably planar.

The present invention provides an alternative to the known prior art and the shortcomings identified. The foregoing and other objects and advantages will appear from the description to follow. In the description reference is made to the accompanying representations, which forms a part hereof, and in which is shown by way of illustration specific embodiments in which the invention may be practiced.

These embodiments will be described in sufficient detail to enable those skilled in the art to practice the invention, and it is to be understood that other embodiments may be utilized and that structural changes may be made without departing from the scope of the invention. In the accompanying illustrations, like reference characters designate the same or similar parts throughout the several views. The following detailed description is, therefore, not to be taken in a limiting sense, and the scope of the present invention is best defined by the appended claims. It will be convenient to hereinafter describe the invention in relation to a metal section in the present exemplary application. However, it is to be appreciated that the invention may be constructed from other materials.

BRIEF DESCRIPTION OF THE DRAWINGS

The present invention will now be described in more detail according to a preferred embodiment but non limiting embodiment and with reference to the accompanying illustrations, wherein.

DETAILED DESCRIPTION

Figure 1:
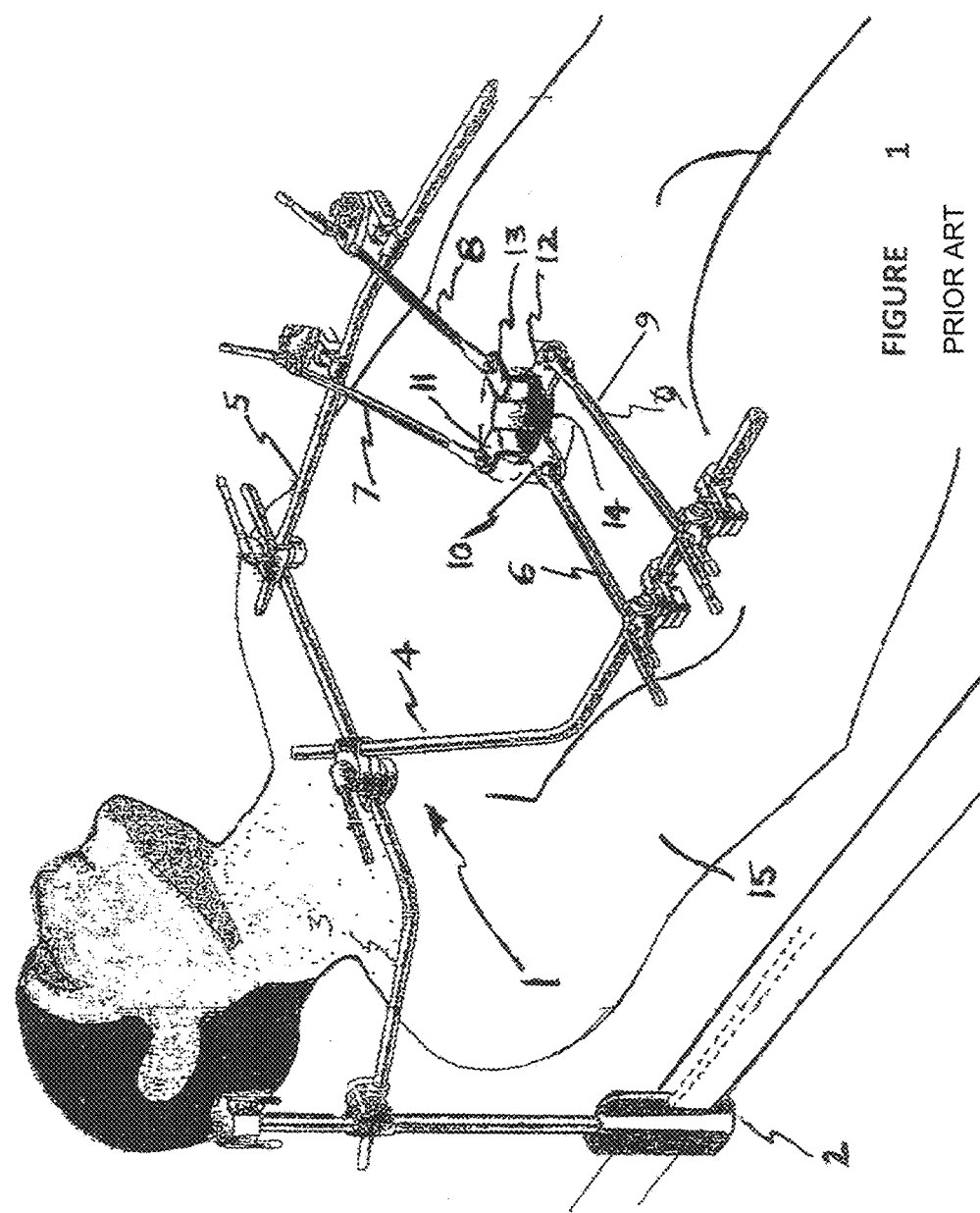
FIG. 1 shows a perspective view of a retraction assembly including a table mounted anchorage and arms retaining a plurality of retractor blades retaining according to a prior art assembly.

Referring to FIG. 1 there is shown, a perspective view of a prior art retraction assembly 1 including a table mounted anchorage 2 supporting primary arm 3 which directly supports secondary arms 4 and 5 and indirectly tertiary arms 6, 7, 8 and 9. Arms 6, 7, 8 and 9 respectively retain a plurality of retractor blades 10, 11, 12 and 13 which penetrate wound 14 of patient 15.

The blade to be described below according to its various embodiments, is capable of adaption to assemblies of the type described in FIG. 1 or alternative retraction assemblies.

Figure 2:
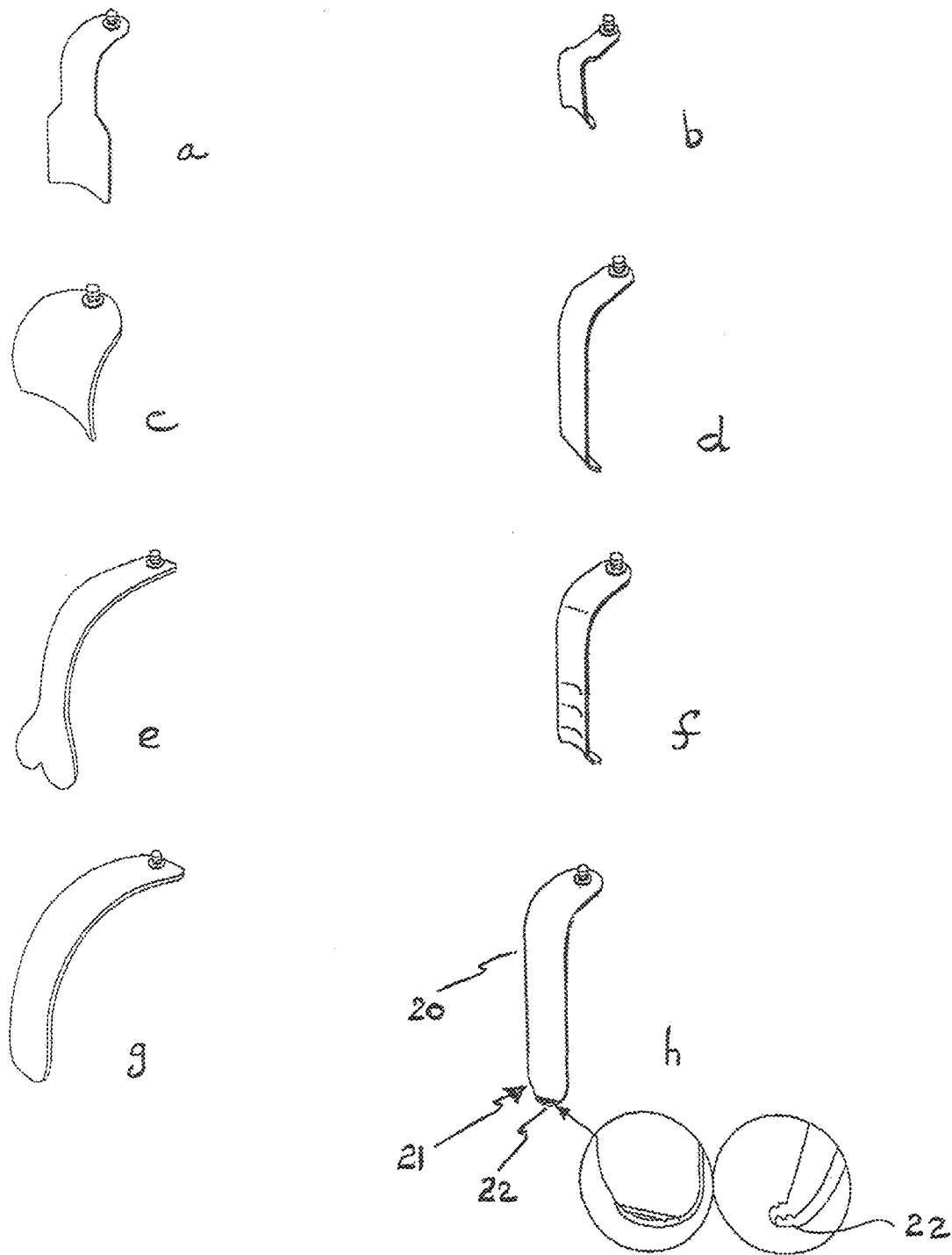
FIG. 2 a-h show perspective views of known retractor blades

FIG. 2 a-h show perspective views of various known retractor blades each having a different geometry but similar fundamental form. Each are typified in having means at a first end for engaging a support assembly a return portion and a distal or second end which is capable of engaging bone or soft tissue, thereby contributing to retraction and support of the blade.

FIG. 2a shows a blade with a geometry that conforms to the anterior spine but in one plane only.

The design objective with retraction blades are primarily, optimal stability and safe and efficient retraction of soft tissue.

The Brau blade 20 shown in FIG. 2h terminates at end 21 in a formation 22 which facilitates bone engagement and therefore anchorage of blade 20.

Contact and pressure on the blade against the bone improves stability of retractor blade 20. Most conventional blades however rely only on their external fixation for stability. These blades effectively "float" with a free end. In the case of the Brau blades which contact bone, the contact is at the side of the vertebral body usually at or above the equator of the vertebrae where the bone is curving posterolaterally.

Formation 22 is in contact with the vertebral bone along a superior inferior plane. To remain stable blade 20 relies primarily on a solid immobile connection to the operating table through various linkages (see FIG. 1) and if in contact with the bone, a radial force is directed via formation 22.

The required stability can be easily achieved by manual engagement of the blade but to a lesser extent when attached to an external frame such as assembly 1 because of the long moment arm from the end of the retractor blade to anchorage 2. Such lateral retractors tend to move and slip causing soft tissues and blood vessels to slip under or around the retractor blades.

Although urging the retractor blade against the bone provides additional stability. The applied force can lead to slipping or sliding anteriorly or posteriorly when the spine moves during heavy disc or bone work. This loss of position can cause tissue injury and frequently requires time consuming adjustments.

Figure 3:
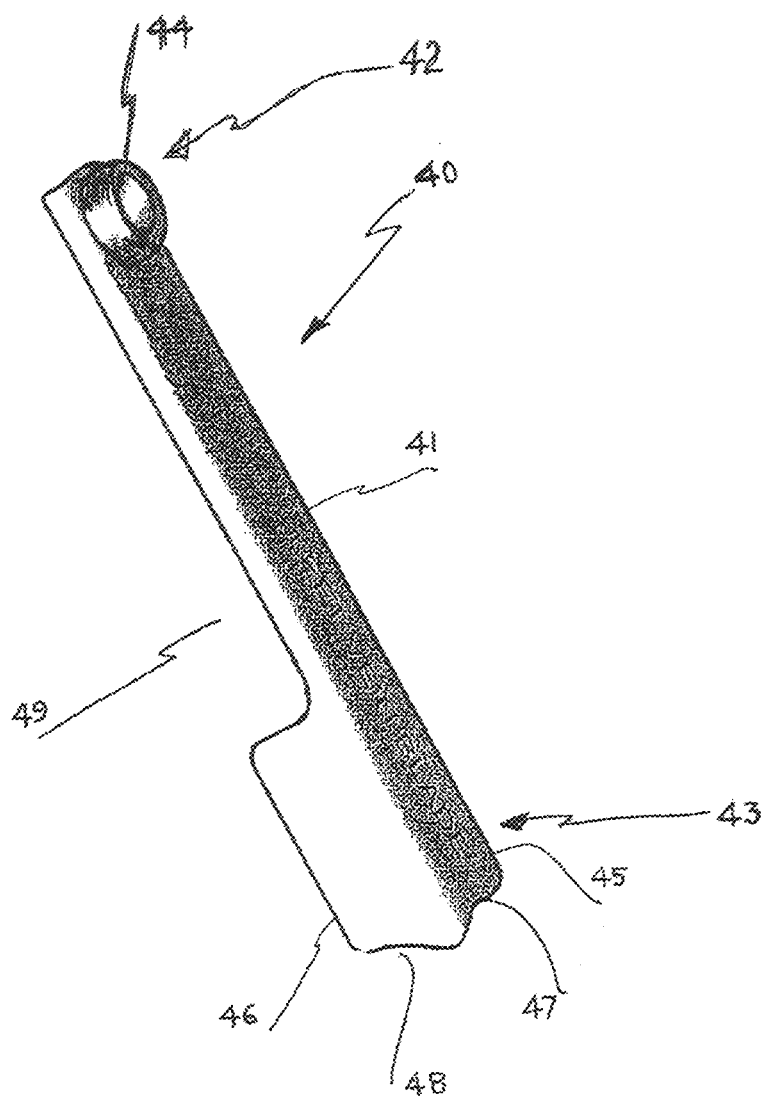
FIG. 3 shows a front perspective view of a retractor blade according to a preferred embodiment.

FIG. 3 shows a front perspective view of a retractor blade 40 according to a preferred embodiment. Blade 40 shown is specifically configured for retraction of left side structures such as veins. Retractor blade 40 comprises: a generally elongated blade body 41 having first end 42 and second end 43. First end 42 provides connection means 44 for connection of the blade body 41 to a support member (not shown). Second end 43 comprises a first part 45 disposed in a first plane and a second part 46 connected to the first part and disposed in a second plane. The first part 45 terminates in an edge 47 at least part of which includes a contour which generally conforms to a contour of a spinal vertebrae at a point of contact with the vertebra when in situ. First part 45 in the first plane is essentially parallel to a longitudinal axis (not shown) of a spine. The second part 46 in the second plane is normal to the first plane and thus normal to the first part 45. The contour of edge 48 of the second part 46 defines an arc which generally conforms to a mid vertebral body circumferential surface. The radius of this arc in the lumbar spine is approximately 45 mm +/−10 mm.

Edges 48 of the second part 46 and edge 47 of the first part 45 engage vertebral bone during insertion and when an axial load is applied to the retractor.

According to one embodiment, the second part 46 is formed by an abbreviation 49 in the body 41 of the blade 40. Preferably, the blade 40 is formed as one piece and a majority of the body of the blade is disposed in the same plane as the first part 45.

Figure 4:
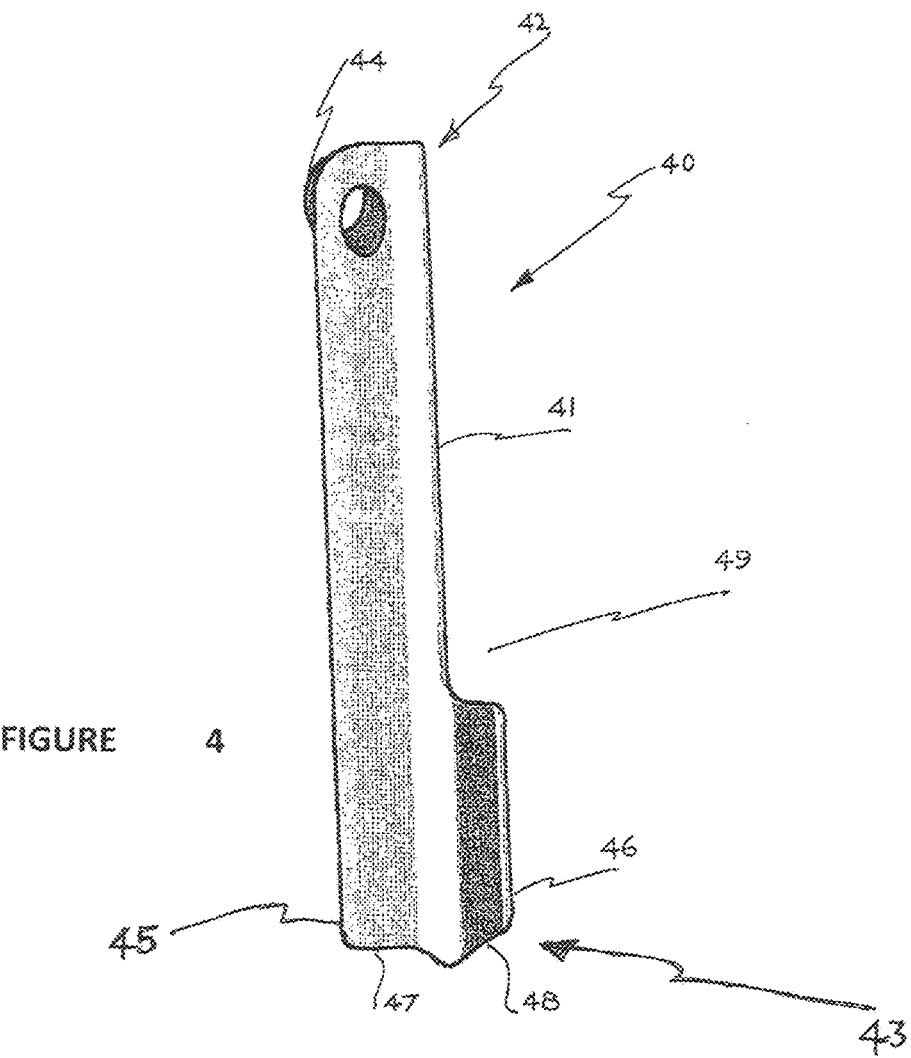
FIG. 4 shows a rear perspective view of the retractor blade of FIG. 3.
Figure 5:
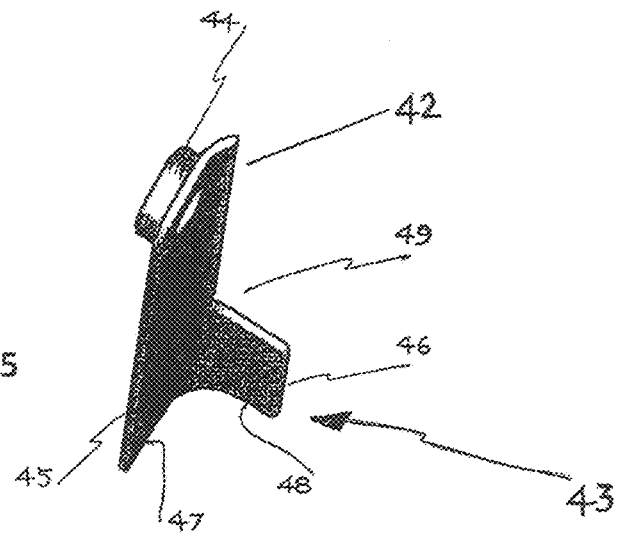
FIG. 5 shows a top perspective view of the blade of FIG. 3.

FIG. 4 shows a rear perspective view of the retractor blade of FIG. 4 with corresponding numbering. FIG. 5 shows a top perspective view of the blade of FIG. 4 with corresponding numbering.

Retractor 40 is configured to maximize contact with the surface of the vertebral bone and to contacting the bone in at least two planes with two of said planes being at right angles to each other. The angled first and second parts 45 and 46 of retractor 40 and contoured edges 47 and 48 approximating the curvature of the vertebra, provide greater stability compared to a flat blade having only a single point contact over the curved surface. By having this conformity in the blade to the curve of the spine provides enhanced resistance to loads applied to retractor blade 40 with reduced tendency for the blade 40 to slip around the curve of the vertebra. A blade with a single point of contact will naturally tend to ride about the circumference of the vertebra even with friction grip provided by a point formation engagement. With contact in at least two planes perpendicular to each other, increased stability for both hand held or table mounted retractors is provided. Since the risk of slippage about the vertebral circumference is eliminated or at least greatly minimized, so is the risk of unwanted blade displacement and slippage producing soft tissue injury.

Figure 6:
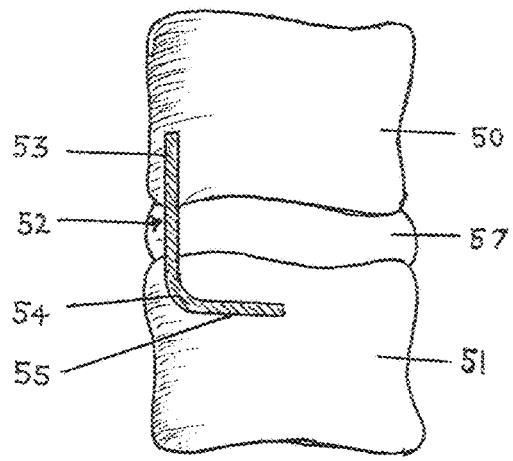
FIG. 6 shows a front plan view of spinal vertebrae with retractor blade engaged.

FIG. 6 shows a top front plan view of spinal vertebrae 50 and 51 with retractor blade 52 engaged. This represents a right handed version of blade type 40 and shows typical position in use at L4/5. The distal end of blade 52 (which corresponds to end 43 of blade 40 of FIG. 4) represents the characterising feature or working contours and surfaces of blade 52. When in use and seen from an anatomical perspective the blade 52 has a first part 53 disposed in a first plane, a curved part 54 and a second part 55 disposed in a plane substantially normal to the first part 53. The shape and configuration of blade 52 causes blade 52 to conform generally to anatomical contours of vertebrae 50 and 51 which according to the illustration shown are right L4/5. The blade 52 is designed ideally to sit with part 55 in contact with bone of vertebrae 51 approximately 5 to 10 mm below the disc space 57.

Figure 7:
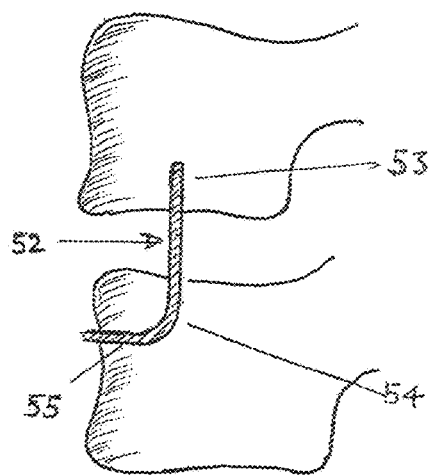
FIG. 7 shows a side view of the spinal vertebrae of FIG. 7 rotated 90 degrees.

FIG. 7 shows a side view of the spinal vertebrae of FIG. 7 rotated 90 degrees.

Figure 8:
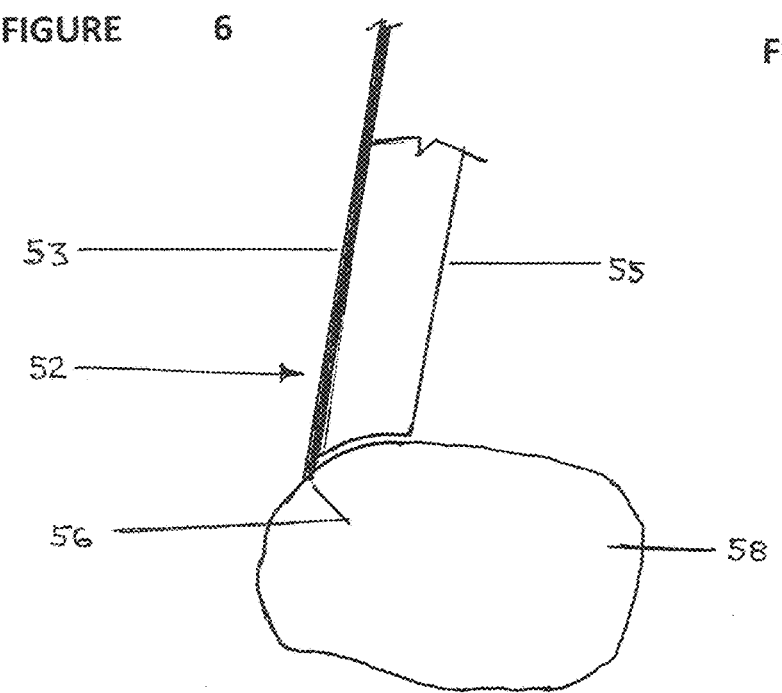
FIG. 8 shows a sectional view of a spinal vertebrae with an elevation view of retractor blade engaged.

FIG. 8 shows a sectional elevation view of a spinal vertebrae 58 with retractor blade 52 engaged. The distal region of the blade 52 and specifically the first part 53 has an edge 56 which terminates in a horizontal curve such that the curve of the lumbar vertebral bodies laterally has radius approximately 45 mm plus/minus 10 mm. To fit other vertebral body curves or in other areas of the spine the curves can be varied accordingly. After a distance of horizontal curvature the blade starts to curve superiorly.

Curved portion 54 which is intermediate respective first and second parts 53 and 55, runs from section 55 superiorly and laterally towards the disc space, gradually becoming the vertical section 53. It conforms to widening of the spine by curving towards the support member and then flattening across and beyond the disc space. As shown in FIG. 8, the curved bottom edge 56 is shaped to remain in contact with the bone as it curves between the first and second parts of the retractor blade 52.

Part 53 has a bottom edge that may have various shapes. Part of sections 53 and 54 of the blade 52 thus remains in contact with the bone or disc wherever on the side of the vertebral body it is positioned, providing at least some bone contact at 90 degrees from the part 55. The Height of the curved and horizontal sections may vary from short to the entire length of the blade but second part 55 is according to a preferred embodiment shown approximately one third of the length of the part 53 of the blade 52 and is formed by an abbreviation to blade 52.

The preferred embodiment of retractor 52 has a smooth curve between right angled planar parts 53 and 55 to provide the additional function of minimizing vessel or tissue distortion whilst providing the required exposure of the disc. An embodiment with two right angled planar plates joined acutely could potentially provide the absolute minimum tissue retraction displacement distance. However this would also produce angular distortion with its risks as, described earlier under the heading: "Bulging and Angular Tissue Distortion".

The preferred embodiment shown improves both retraction of blood vessels, protection by filling in the corners when compared to two separate retractor blades normal to each other. This provides complete coverage of the vessel in its most exposed and hazardous position.

Figures 9, 10:
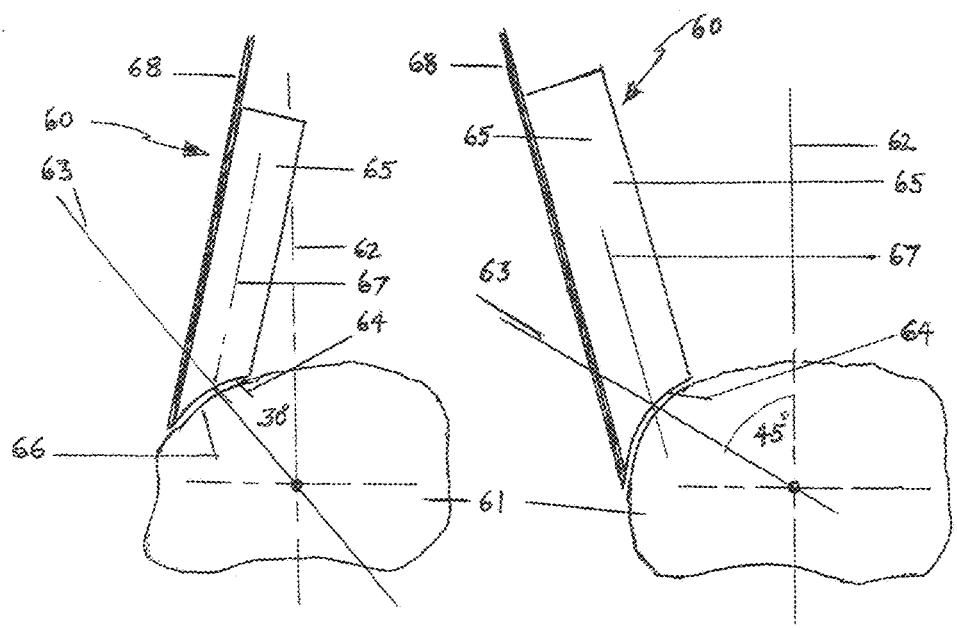
FIG. 9 shows a sectional elevation view of a spinal vertebrae with retractor blade engaged in a first orientation towards a midline of a spinal vertebrae.
FIG. 10 shows the sectional elevation view of FIG. 10 of the spinal vertebrae with retractor blade engaged and disposed in a second orientation rotated anticlockwise relative to the orientation of FIG. 9.

FIG. 9 is a representation of an initial position of a retractor blade 60 before full tissue retraction and shows a sectional elevation view of a spinal vertebrae 61 with retractor blade 60 engaged in a first radial orientation leaning towards a midline 62 of a spine. The angle of repose of retractor blade 60 is shown relative to midline 62. Curved surface 64 of blade part 65 engages and at least partially confirms to curved region 66 of vertebrae 61, with the part 65 fully in contact with the bone of vertebrae 61. Midline 67 of part 65 intersects a radial line 63 which is disposed at approximately 30 degrees from mid line 62 of vertebrae 61. Retractor blade 60 part 65 is disposed normal to part 68.

FIG. 10 shows the sectional elevation view of FIG. 9 of the spinal vertebrae with retractor blade engaged and disposed in a second orientation. Retractor 60 is shown rotated anti clockwise around vertebrae 61 to a position in which vertebrae 61 is sufficiently exposed and soft tissues are fully retracted for performance of surgery.

Figures 11, 12:
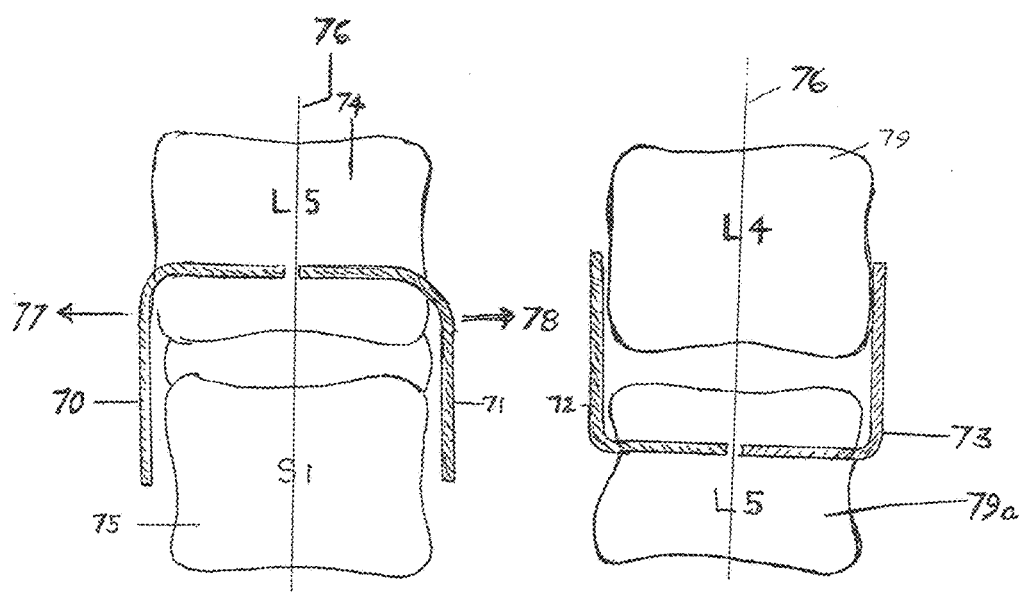
FIG. 11 shows an L5 vertebrae and S1 with opposing blades engaged to L5.
FIG. 12 shows an L5 vertebrae and S1 with opposing blades engaged to L5.

In a typical procedure, exposure of the anterior spine is performed in the usual way dividing any tethering veins (usually segmental or iliolumbar vein). The disc is partially exposed and then the right sided retractors are inserted into position with the circumferential curve located corresponding to curve 64 just below the L4/5 disc but in the midline or to the left. Retractor 60 may be located initially in the orientation shown in FIG. 9 then rotated and moved laterally from right to left relative to midline 62 to adopt the attitude shown in FIG. 10 but remaining in bony contact with vertebrae 61 throughout its rotation and at the same time displacing the common iliac vein. The finished working position for retractor 60 is shown in FIG. 10 approximately 45 degrees from the vertical midline 62. By having the main axis of the blade 61 at 30 degrees from the radius keeps blade 61 optimally positioned with 15 degrees of outward slope which provides a desirable extent of retraction. Variations in this 30 degree angle are envisaged. Blade 60 will typically be manufactured in left and right side versions. It is envisaged that using a left and right blade together on either sides of the spine would create a trough shape across the spine between the disc and the vessels, thoroughly protecting them during L4/5 surgery. A similar technique to that described above in FIGS. 9 and 10 can be used on the right had side for an opposing retractor blade at L4/5. FIG. 11 shows an L5 vertebrae 74 and 75 S1 with opposing blades 70 and 71 engaged with bone. At L5/S1 the retractors 70 and 71 are initially positioned relative to midline 76 and then each respectively slid and rotated separately or together from centre to left and centre to right in the direction of arrows 77 and 78. During L5/S1 surgery where the vessels typically lie above the disc space, the left and right configuration would be reversed creating a dome type shape protecting the vessels as they pass around and over the disc space.

FIG. 12 shows an L4 vertebrae 79 and L5 vertebrae 79a with opposing blades 72 and 73 engaged relative to midline 76.

In another embodiment of a right Angled Version, an increased contact with the bony vertebral surface could be achieved in more than one plane with two perpendicular sections joined at a right angle, but this would indent the tissues more acutely rather than with the smoother curve as shown in the representations. The smooth curve joining the two is a preferred but non limiting embodiment.

Figure 13:
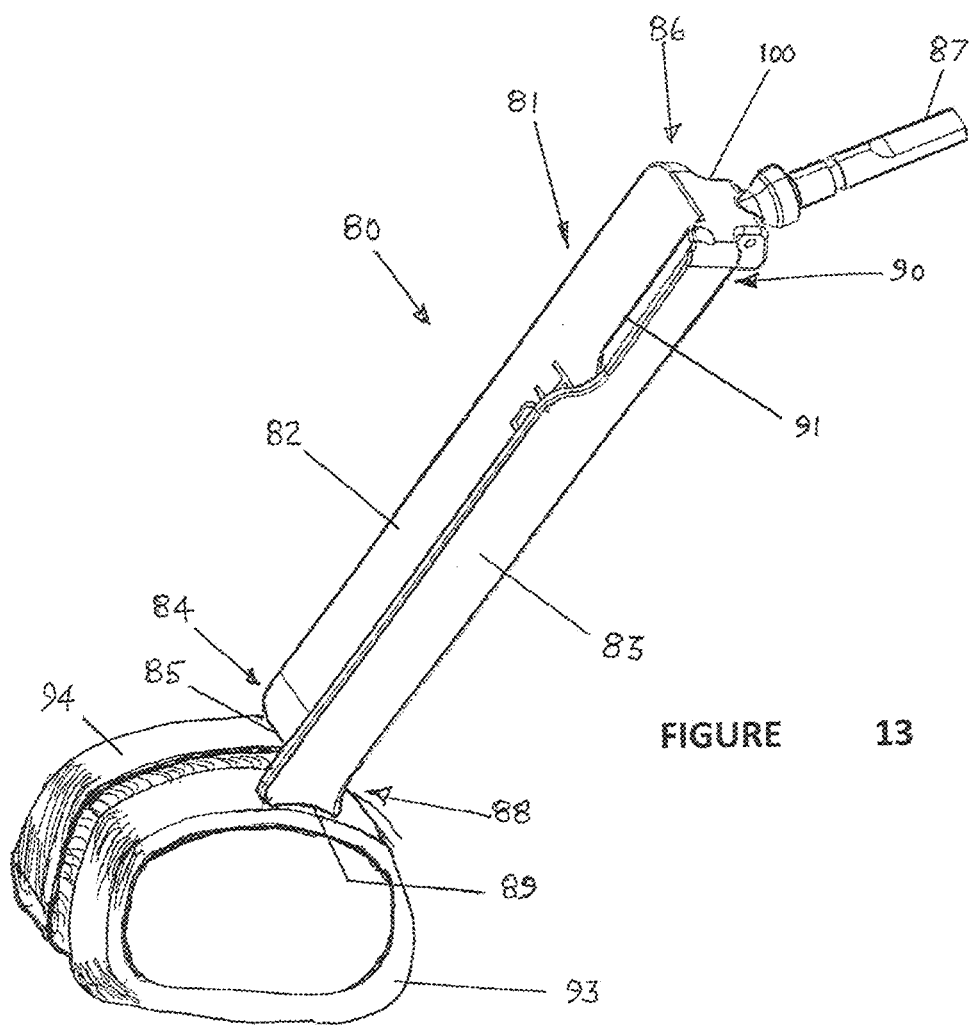
FIG. 13 shows a perspective view of a retractor blade according to an alternative embodiment.

FIG. 13 shows a perspective view of a retractor blade 80 according to a preferred embodiment. Blade 80 comprises an angled body 81 comprising first planar leg 82 and second planar leg 83. Leg 82 terminates at distal end 84 in a curved formation 85 which in use engages vertebral bone. Opposite end 86 receives retains via mounting block 100 a mounting arm 87 which when the retractor blade 80 is in use engages a supporting structure which retains retractors. Leg 83 terminates at end 88 in curved formation 89 which engages bone when retractor blade 80 is in use. Leg 83 terminates at end 90 in an abbreviation 91.

At least part of formation 89 of leg 83 confirms generally to the contoured surface 92 of vertebrae 93. Likewise at least part of formation 85 conforms to at least part of a contour of surface 94 of vertebrae 93.

Figure 14:
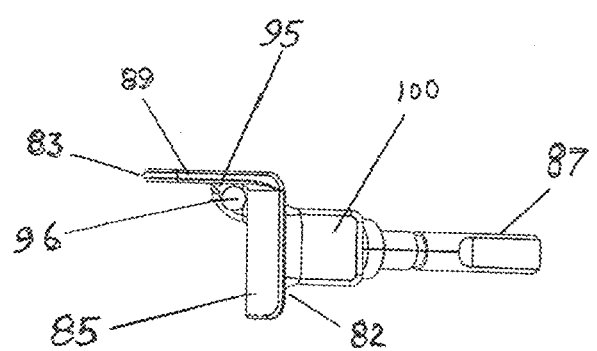
FIG. 14 shows an end view of the retractor blade of FIG. 13.

FIG. 14 shows with corresponding numbering a bottom view of the retractor blade 80 of FIG. 13. From the top view it may be seen that retractor blade 80 further comprises cannulation 95 which includes opening 96 which receives an anchor pin (see FIG. 15) for fixing retractor to vertebrae 101.

Figure 15:
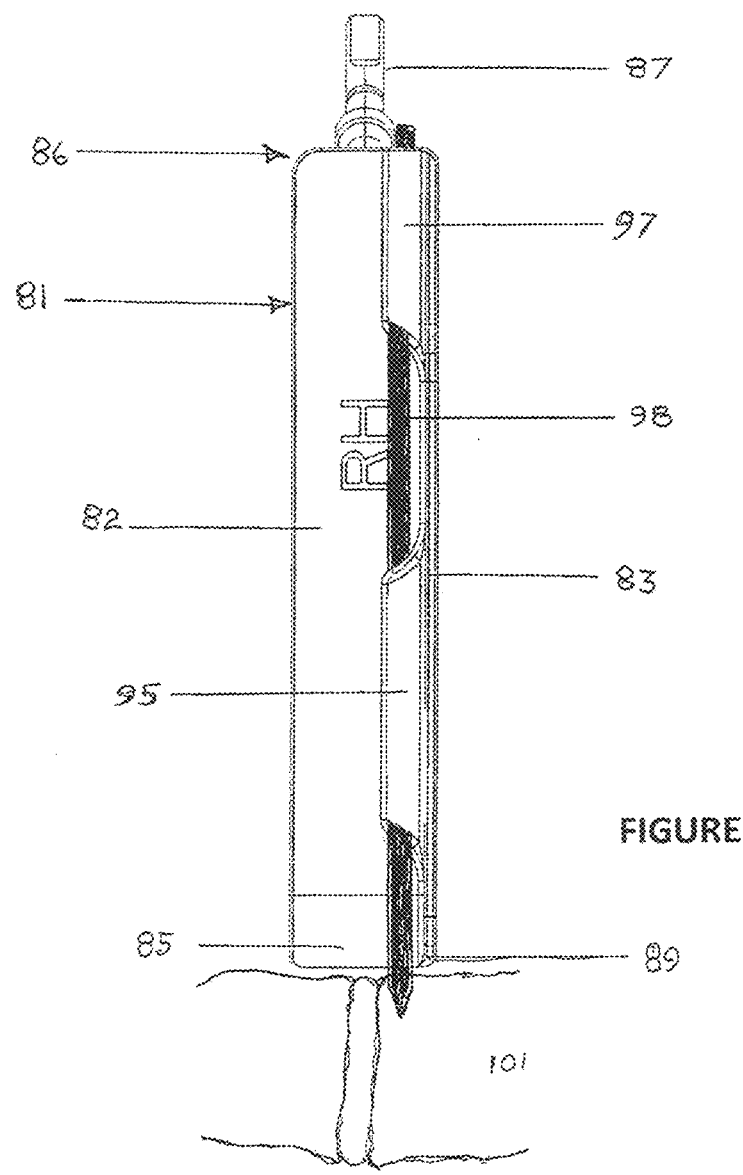
FIG. 15 shows a front elevation view of the retractor blade of FIG. 13.

FIG. 15 shows with corresponding numbering a front elevation view of the retractor blade 80 of FIG. 13 further comprising sleeve cannulations 95 and 97 which in use, receives retaining pin 98. Such cannulations are known in existing retractor blades but not in a blade having the geometry of the distal end formations as described. The passage through the cannulations preferably lies parallel to a long axis of the inside of the curved, horizontal or vertical section of the blade and on the inside of the curved portion. An alternative to a channel would include a small simple ring flange at right angles to the bottom edge 89 of the blade 80 sitting on or close to the bone that allows securing of the retractor 80 with a screw or short pin (not shown) to the spine once in position. Such a flange may hinge or rotate either parallel to a leading edge of the blade or normal to it allowing some adjustment to achieve best bony contact. The flange could be at any position along the leading (distal) edge of blade although a preferred embodiment for flange would be from end 88 allowing vertical entry of screw or pin. Other known means of securing to the spine are also contemplated. Leg 83 has at end 90 an abbreviation 91 and at opposite end 88 terminates in a radiused portion 89.

Figure 16:
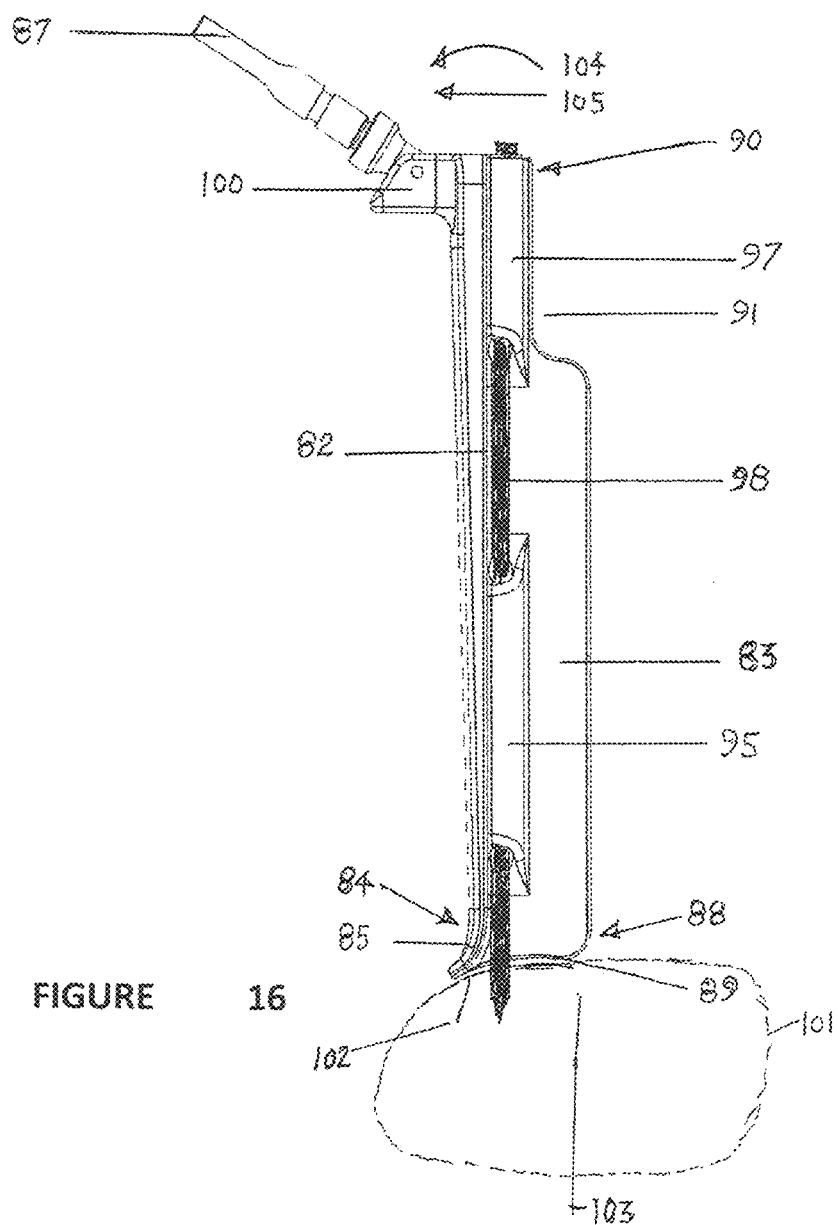
FIG. 16 shows a side elevation view of the retractor blade of FIG. 13.

FIG. 16 shows with corresponding numbering a side elevation view of the retractor blade 80 of FIG. 13. From this view it may be seen that leg 82 terminates at end 84 in a curved formation 85 which in use engages contoured surface 102 of vertebral bone 101. Formation 85 is preferably a swept back curve which presents a potentially greater bone engaging surface than would be the case with a straight edge. This allows end 84 and more particularly formation 85 to track around the bone more easily when a surgeon is urging the retractor 80 away from the mid line 103 of vertebrae 101 for required retraction. Pin 98 is set once the final location for the retractor is established. Leg 83 terminates at end 88 in curved formation 89 which engages bone surface 102 when retractor blade 80 is in use. Since formation 89 is curved this allows the retractor to confirm to the bone contour and also assists tracking of the retractor 80 when it is urged towards a full retraction position. Movement of retractor 80 will be usually a combination of rotation in the direction of arrow 104 and lateral displacement in the direction of arrow 105.

Retractor blade 80 may be adapted with a handle whose longitudinal axis is positioned in line with the curved portion to align the centre of gravity with this edge thereby improving the balance and control of the distal end of the blade.

The blade assembly described herein in each embodiment may be adapted to known retractor blades. i.e formations may be introduced into existing retractor blades. Thus a blade may be detachable or malleable, rotating and other variable engagements are envisaged. Blades may also be separate from a handle to allow fixation of the blade at various angles as known in the prior art.

Various materials may be used for the retractor including metals and plastics and malleable and radiolucent materials. Various sizes and shapes are envisaged.

The invention is characterized in a retractor having two orthogonal plates (first and second parts) in contact with the bone. The retractor is preferably shaped to fit a spine in at least 2 orthogonal planes, joined by intermediate section also curved to contact the bone.

Unlike known blades where the main axis of blade is orthogonal to a distal edge, the blade according to the invention includes a section at an angle to fit to a spine without requiring enlargement of a surgical wound to accommodate the blade. The retractor is specifically designed with smooth curves to protect vessels while retracting and while held in fixed position and has the added advantage of reduced tissue distortion and improved retraction.

Variations in the retractor may be made to accommodate different variation in engagement to vertebrae. For instance the length, width and relative heights of horizontal and vertical sections, may vary to accommodate, different locations in the spine and different types of procedures. Also, corners of the device may be radiused and in the lumbar spine build up sections over the corners added in order to retract blood vessels.

It will be further recognised by persons skilled in the art that numerous variations and modifications may be made to the invention without departing from the overall spirit and scope of the invention broadly described herein. Such modifications would allow adaptation of key concepts to provide locking of distraction devices for use in anterior or posterior spinal surgery throughout the length of a spine or in orthopaedics or other surgical disciplines where bony fixation is available.

The claims defining the invention are as follows:

1. A retractor blade, comprising:
a blade body having first and second ends, the first end of the blade body facilitating connection of the blade body to a blade support member, the second end of the blade body including a first part disposed in a first plane and a second part connected to the first part and disposed normal to the first part in a second plane, and
wherein the first part terminates at a distal end that includes a radiused convex contour that extends in a direction away from the second part and beyond the first plane to allow the radiused convex contour of the distal end of the first part to oppose and conform to a first contour of vertebral bone, and
wherein the second part terminates in a distal end edge that includes a concave contour that at least partially conforms to a second contour of the vertebral bone.

2. A retractor blade according to claim 1, wherein, when the retractor blade engages the vertebral bone under load, the distal end edge of the second part and a distal end edge of the first part are normally disposed to one another, and the concave contour of the end edge of the second part and the distal end of the first part engage the vertebral bone to conform to the first and second contours of the vertebral bone simultaneously.

3. A retractor blade according to claim 2, wherein at least part of the retractor blade is L shaped for at least part of a full length of the retractor blade.

4. A retractor blade according to claim 3, wherein the second part includes an abbreviation at a proximal end of the retractor blade extending distally from the first end for at least part of the full length of the retractor blade.

5. A retractor blade according to claim 4, wherein the radiused convex contour of the first part has a convex inner surface that engages the first contour of the vertebral bone and a concave outer surface.

6. A retractor blade according to claim 5, wherein the concave contour of the distal end edge of the second part cooperates with the radiused convex contour of the first part when load is applied to the retractor blade.

7. A retractor blade according to claim 6, wherein the radiused convex contour of the first part engages a circumferential region of a vertebra in a longitudinal axial direction and the concave contour of the distal end edge of the second part engages the same vertebra along a line that is normal to a longitudinal axis.

8. A retractor blade according to claim 7, further comprising at least one cannulation extending for at least a part of a length of a longitudinal junction of the first and second parts.

9. A retractor blade according to claim 8, wherein a first cannulation is disposed at the proximal end and a second cannulation is disposed at a distal end of the retractor blade.

10. A retractor blade according to claim 9, wherein each cannulation includes a through passage which receives a bone anchor.

11. A retractor blade according to claim 10, wherein a mounting block allows connection of the blade to a support member, and wherein the mounting block receives and retains a mounting arm.

12. A retractor blade according to claim 11, wherein the mounting block is mounted on an outside surface of the first part of the retractor blade.

13. A retractor blade according to claim 12, wherein the retractor blade is manufactured from titanium.

14. An L shaped retractor blade for retracting soft tissues during spinal surgery, the retractor blade comprising:
a blade body having first and second ends, the first end allowing connection of the blade body to a support member, the second end comprising a first part disposed in a first plane and a second part disposed in a second plane normal to the first plane, and
wherein each of said first and second parts terminate in a respective radiused contour at least part of which is capable of transmission of load applied to the retractor blade to spinal vertebrae when the second end of the blade body engages the spinal vertebrae, and
wherein each respective radiused contour of the first and second parts of the blade body conforms to at least part of contours of said vertebrae to provide a resisting force to restrain unwanted movement of the retractor blade during retraction by the retractor blade of soft tissue,
wherein the first part terminates at a distal end that includes a radiused convex contour that extends in a direction away from the second part and beyond the first plane to allow the distal end of the first part to at least partially conform to an opposing first contour of vertebral bone, and
wherein the second part terminates in an end edge that includes a concave contour that at least partially conforms to and opposes a second contour of the vertebral bone.

* * * * *